United States Patent [19]

Walraven et al.

[11] Patent Number: 5,164,519

[45] Date of Patent: Nov. 17, 1992

[54] PROCESS FOR THE SEPARATION OF R AND S-2,2-$R_1$,$R_2$-1,3-DIOXOLANE-4-CARBOXYLIC ACID

[75] Inventors: Hubertus G. M. Walraven, Schipluiden; Paulus B. M. Groen, Spijkenisse; Everardus J. A. M. Leenderts, Rhoon, all of Netherlands

[73] Assignee: Shell Internationale Research Maatschappij B.V., The Hague, Netherlands

[21] Appl. No.: 801,437

[22] Filed: Dec. 2, 1991

Related U.S. Application Data

[63] Continuation of Ser. No. 625,937, Dec. 11, 1990, abandoned, which is a continuation-in-part of Ser. No. 472,618, Jan. 30, 1990, abandoned.

[30] Foreign Application Priority Data

Nov. 1, 1989 [EP] European Pat. Off. .......... 89 202765

[51] Int. Cl.$^5$ ............................................. C07D 317/26
[52] U.S. Cl. ..................................... 549/450; 549/342
[58] Field of Search ................................ 549/450, 342

[56] References Cited

U.S. PATENT DOCUMENTS 4,575,558  3/1986  Mai ...................... 549/453
4,745,200  5/1988  Moeller .................. 549/450

FOREIGN PATENT DOCUMENTS 189586  8/1986  European Pat. Off. .
217375  4/1987  European Pat. Off. .

OTHER PUBLICATIONS

Ruholl et al., Synthesis 1, 1988, pp. 54-55.

*Primary Examiner*—Nicky Chan
*Attorney, Agent, or Firm*—Bierman and Muserlian

[57] ABSTRACT

A process is disclosed for preparing a 2,2-$R_1$, $R_2$-1,3-dioxolane-4-carboxylic acid or salt thereof rich in either the R or S enantiomer which process comprises a) preparing a solution which contains a non-racemic mixture of R and S enantiomer of a carboxylate of the formula

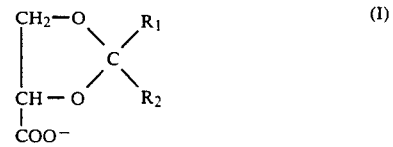

and $M^{n+}$ ions, wherein $R_1$ and $R_2$ are each, independently, H or an unsubstituted or substituted alkyl group, or $R_1$ and $R_2$, together with the carbon atom to which they are attached, form an unsubstituted or substituted carbocyclic ring, and M is an alkali metal, an alkaline earth metal, a group IIb metal, boron, or an ammonium, di- or trialkanolammonium ion having 2 or 3 carbon atoms or a tetra $C_1$-$C_{16}$ alkyl ammonium ion, and n is the valency of M;

b) reducing the solubility of the $M^{n+}$ salt of compound (I); and c) separating the resulting crystals from the mother liquor.

6 Claims, No Drawings

PROCESS FOR THE SEPARATION OF R AND S-2,2-$R_1$,$R_2$-1,3-DIOXOLANE-4-CARBOXYLIC ACID

This application is a continuation of U.S. patent application Ser. No. 625,937 filed Dec. 11, 1990, now abandoned which was a continuation-in-part application of Ser. No. 472,618 filed Jan. 30, 1990, now abandoned.

The present invention relates to the separation of 2,2-$R_1$,$R_2$-1,3-dioxolane-4-carboxylic acid and its salts into its enantiomers and to the compounds thus obtained.

Both enantiomers of 2,2-dimethyl-1,3-dioxolane-4-carboxylic acid are important starting materials for the preparation of agricultural and pharmaceutical products, see for example J. Jurczak et al., Tetrahedron Vol. 42, no. 2, 447–488 (1986).

In recent years, the enantiomers of 2,2-$R_1$,$R_2$-1,3-dioxolane-4-carboxylic acid have become of interest since they are important starting or intermediate compounds for the preparation of many biologically active products, especially for the preparation of chiral drugs. The preparation of biologically active products in optically pure form using chiral starting materials or intermediates is very advantageous, enabling precise planning and efficient realization of synthetic pathways.

The enantiomers of 2,2-$R_1$,$R_2$-1,3-dioxolane-4-carboxylic acid are important examples of $C_3$-synthons and can be used as starting compounds for the preparation of many other $C_3$-synthons which are widely applied in organic synthesis as chiral building blocks. For example, R and S-2,2-dimethyl-1,3-dioxolane-4-carboxylic acid can be used in the synthesis of other chiral synthons, monosaccharides, their derivatives and other polyhydroxyl systems, and biologically active products of more complex structure. Examples of the syntheses of such complex structures include the preparation of β-blockers or optically pure β-lactam systems.

H. Ruholl (Synthesis Jan. 1, 1988, p. 54) describes the preparation of the optical pure enantiomers of the potassium salt of 2,2-dimethyl-1,3-dioxolane-4-carboxylic acid. The isomers are formed by the oxidative cleaving of the chiral 1,2:5,6-di-O-isopropylidene-D-mannitol or 5,6-O-isopropylidene-L-ascorbic acid by electrolysis at an oxide covered nickel electrode. However, this process starts with a pure isomer.

In EP-A-0244912 a microbial process is disclosed in which, starting from an R,S mixture of 2,2-$R_1$,$R_2$-1,3-dioxolane-4-methanol, R-2,2-$R_1$,$R_2$-1,3-dioxolane-4-carboxylic acid is produced by the microbial stereoselective oxidation of S-$R_1$,$R_2$-1,3-dioxolane-4-methanol. The R-acid thus formed shows an enantiomeric excess of about 90%. However, higher purities are demanded upon chiral starting compounds.

There is therefore still a great need for a process which may be used on an industrial scale, which allows economically attractive yields of the R and S enantiomers of 2,2-dimethyl-1,3-dioxolane-4-carboxylic acid to be produced from a mixture of the compound. The present invention provides such a process.

It has been surprisingly found that a 2,2-$R_1$,$R_2$-1,3-dioxolane-4-carboxylic acid or salt thereof which is enriched in either its R or S enantiomer can be prepared by selective crystallization of the enantiomer which is in excess present in the solution.

Accordingly, the present invention provides a process for preparing a 2,2-$R_1$,$R_2$-1,3-dioxolane-4-carboxylic acid or salt thereof rich in either the R or S enantiomer which process comprises a) preparing a solution which contains a non-racemic mixture of R and S enantiomer of a carboxylate of the formula

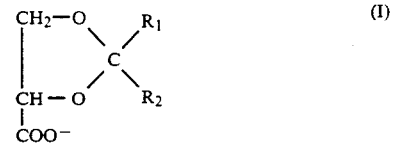

and $M^{n+}$ ions, wherein $R_1$ and $R_2$ are each, independently, H or an unsubstituted or substituted alkyl group, or $R_1$ and $R_2$, together with the carbon atom to which they are attached, form an unsubstituted or substituted carbocyclic ring, and M is an alkali metal, an alkaline earth metal, a group IIb metal, boron, or an ammonium, di- or tri-alkanolammonium ion having 2 or 3 carbon atoms or a tetra $C_1$-$C_{16}$ alkyl ammonium ion, and n is the valency of M;

b) reducing the solubility of the $M^{n+}$ salt of compound (I); and c) separating the resulting crystals from the mother liquor.

Hereafter, if desired, the salt enriched in one isomer can be converted in its corresponding acid.

If the starting solution contains an excess of R isomer, crystals enriched in the R isomer are formed, if the starting solution contains an excess of S isomer, crystals enriched in the S isomer are formed. It has been found that the quantity of the excess of one isomer in relation to the other isomer in the starting solution corresponds to the maximum amount of crystals that can be formed in that isomer. After crystallization the mother liquor will ultimately contain a racemic mixture of the compound in question. Often however in industrial processes the crystallization will not be complete and the final mother liquor will still contain an (smaller) excess of the isomer in question.

Advantageously, $R_1$ and $R_2$ are each a branched or unbranched $C_1$-$C_6$ alkyl group or $R_1$ and $R_2$, together with the carbon atoms to which they are attached, form an unsubstituted or substituted carbocyclic ring containing 8 carbon atoms or less.

Preferably $R_1$ and $R_2$ are identical. In this way no extra asymmetry is brought into the compounds.

More preferably, $R_1$ and $R_2$ are each a $C_1$-$C_4$ alkyl group or, together with the carbon atoms to which they are attached, $R_1$ and $R_2$ form a carbocyclic ring containing 5 to 6 carbon atoms. In a preferred embodiment $R_1$ and $R_2$ are both methyl.

The process of the invention involves preparing a solution which contains a mixture of the R and S enantiomer of the carboxylate of formula (I) and at least a substantial amount of the metal M in ion form ($M^{n+}$). This solution is prepared by any conventional method, for example by dissolving the corresponding acid of compound (I) together with M in ion form, as separate compounds, or by dissolving the M-carboxylate directly. The solution advantageously contains an excess of M in ion form compared to the stoichiometrical amount of compound (I).

Typically, M is Na, K, Ca, Mg, Zn or Ba; and preferably M is Na, K, Ca, Ba or Zn.

The solubility of the M-salt of compound (I) in the solution is reduced by conventional means, such as by adjusting the pH, by evaporating part of the solvent, by adding another solvent, by decreasing the temperature of the solution or by any other known method or combinations thereof. This promotes crystallization of the enantiomer of compound (I) which is in excess compared to the other. During or after this solubility reduction it is possible to add seeding crystals (of the isomer in question) to the solution. With the present process it becomes possible to obtain precipitates of compound (I) in the preferred form with an e.e. of at least 90%, preferably of at least 95% and more preferably of about 99% (98–99.9%).

An excess of $M^{n+}$ can also be used to reduce the solubility of the M-salt of compound (I). For example, super-saturation-conditions can be created by adding extra M in ion form.

The crystallization in accordance with the invention takes place within a broad temperature range which is determined, as the skilled person will appreciate, by the physical properties of the particular salt of compound (I) being formed and by the solvents used. In practice, a temperature from $-50°$ C. to $+100°$ C. is used. More preferably, temperatures from $-20°$ C. and $+100°$ C. are applied. The pH during crystallization is typically maintained from 3 to 14, more preferably from 6 to 10.

All publications and patent applications cited in this specification are herein incorporated by reference as if each individual publication or patent application were specifically and individually indicated to be incorporated by reference.

The present invention will be further illustrated by the following Examples. These examples are provided for illustrative purposes only and are not to be construed as limiting the scope of this invention.

It will be readily apparent to those of ordinary skill in the art in light of the teachings of this invention that certain changes and modifications may be made thereto without departing from the spirit and scope of the appended claims.

EXAMPLE 1

Crystallization of the calcium salt of 2,2-dimethyl-1,3-dioxolane-4-carboxylic acid 10.0 g of anhydrous $CaCl_2$ and 25.0 g of sodium 2,2-dimethyl-1,3-dioxolane-4-carboxylate (content of 85.7% calculated as free acid and 78% e.e. in R-form) were dissolved in 165 ml of methanol. The resulting mixture was stirred at 25° C. for 17 hours. The precipitated NaCl was filtered off and 250 ml of acetone was added to the filtrate. Subsequently 16 ml of demineralized water was added to the clear solution initiating the crystallization of the desired product. The resulting slurry was stirred for 24 hours and filtered over a sintered glass funnel. The product was washed with 40 ml of a mixture of methanol, acetone and water (32:50:3) and dried for 17 hours at 30° C.

Yield: 23.6 g of calcium 2,2-dimethyl-1,3-dioxolane-4-carboxylate.3 $H_2O$ (content of 75.5% calculated as free acid and 96% e.e. in R-form).

4.00 g of this salt was recrystallized from 17 ml of refluxing methanol. After cooling to 20° C. the product was filtered over a sintered glass funnel, washed with 5 ml of methanol and dried for 17 hours at 30° C.

Yield: 1.95 g of calcium 2,2-dimethyl-1,3-dioxolane-4-carboxylate.3 $H_2O$ (content of 76.1% calculated as free acid and >99% e.e. in R-form).

The percentage of R and S of the 2,2-dimethyl-1,3-dioxolane-4-carboxylic acid or its salts was determined according to the following method. A solution of 40 mg of the salt in 1.0 ml of a phosphate buffer (pH=2.0) is extracted with 1.0 ml of $CDCl_3$ and filtered over $MgSO_4$. In the $^1H$-(360)-NMR spectrum of this solution the positions of 2,2-dimethylprotons are 1.44 and 1.56 ppm. After addition of 50 μl of a solution of R-(+)-1-(1-naphtyl)ethylamine (200 mg and 1.0 ml of $CDCl_3$) the positions of these protons shift to 1.0 and 1.1 ppm for the R-isomer and to 1.2 and 1.3 ppm for the S-isomer.

EXAMPLE 2

Crystallization of the calcium salt of 2,2-dimethyl-1,3-dioxolane-4-carboxylic acid 2 l of an aqueous solution of 96 g of sodium 2,2-dimethyl-1,3-dioxolane-4-carboxylate (content of 78.0% calculated as free acid and 82% e.e. in R-form) was concentrated under reduced pressure to a volume of 500 ml. After addition of 1500 ml of methanol and 80 g of filter-aid the solution was stirred for another 15 minutes and filtered. The filter-cake was washed with 200 ml of methanol. The total filtrate was added slowly to a solution of 40 g of $CaCl_2$ in 100 ml of water. During this addition, methanol was distilled off under atmospheric pressure. The residue, with a volume of 500 ml containing a crystalline mass was cooled to 0°–5° C. and stirred for 2 hours. The product was isolated over a sintered glass funnel and washed with 200 ml of a mixture of methanol and water (1:3), and dried at 50° C. for 18 hours.

Yield: 77 g of calcium 2,2-dimethyl-1,3-dioxolane-4-carboxylate.3 $H_2O$ (content of 74% calculated as free acid and with 98% e.e. in R-form).

EXAMPLE 3

Crystallization of the calcium salt of 2,2-dimethyl-1,3-dioxolane-4-carboxylic acid Under continuous stirring at 20° C., 1.5 l of a 50% (w/v) solution of $CaCl_2$ in water was added to 20 l of an aqueous solution of 2.24 kg of sodium 2,2-dimethyl-1,3-dioxolane-4-carboxylate (content of 78% calculated as free acid and 76% e.e. in R-form). After 14 hours the crystallized product was filtered off, washed with acetone and dried at 70° C.

Yield: 1.72 kg of calcium 2,2-dimethyl-1,3-dioxolane-4-carboxylate.3 $H_2O$ (content of 71.8% calculated as free acid and >98% e.e. in R-form).

The mother liquor having a volume of about 18 l, still contained 900 g of 2,2-dimethyl-1,3-dioxolane-4-carboxylic acid (46% e.e. in R-form) as a mixture of its calcium and sodium salts.

200 ml of the above mentioned $CaCl_2$ solution was added to 2 l of the mother liquor. After seeding with a few mg of the first crop of crystals and stirring for 4 days at 20° C., the precipitate was isolated analogously as described above.

Yield: 45 g of calcium 2,2-dimethyl-1,3-dioxolane-4-carboxylate (content of 79% calculated as free acid and 96% e.e. in R-form).

In the second mother liquor there was left 54 g of 2,2-dimethyl-1,3-dioxolane-4-carboxylic acid (14% e.e. in R-form) as a mixture of its calcium and sodium salts.

EXAMPLE 4

Crystallization of the calcium salt of 2,2-dimethyl-1,3-dioxolane-4-carboxylic acid 4.0 g of anhydrous $CaCl_2$ and 10.0 g of crude sodium 2,2-dimethyl-1,3-dioxolane-4-carboxylate (content of 78.0% calculated as free acid and 79% e.e. in R-form) was dissolved in 50 ml of methanol. After stirring for one hour this solution was filtered over a sintered glass funnel and 25 ml of aceton and 70 ml of water were added to the filtrate. After crystallization, the stirring was continued for an hour and the slurry was isolated over a sintered glass funnel. The product was dried for 17 hours at 30° C.

Yield: 6.2 g of calcium 2,2-dimethyl-1,3-dioxolane-4-carboxylate.3 $H_2O$ (content of 76.7% calculated as free acid and 98% e.e. in R-form).

EXAMPLE 5

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 9.0 g of sodium (R)-2,2-dimethyl-1,3-dioxolane-4-carboxylate and 1.0 g of potassium (S)-2,2-dimethyl-1,3-dioxolane-4-carboxylate (content of 82.7% calculated as free acid and 81% e.e. in R-form) in 90 ml of methanol. After crystallization the stirring was continued for 17 hours and the slurry was filtered over a sintered glass funnel. The product was dried for 17 hours at 30° C.

Yield: 7.7 g of calcium 2,2-dimethyl-1,3-dioxolane-4-carboxylate.3 $H_2O$ (content of 73.0% calculated as free acid and 98% e.e. in R-form).

EXAMPLE 6

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 8.0 g of sodium (R)-2,2-dimethyl-1,3-dioxolane-4-carboxylate and 2.0 g of potassium (S)-2,2-dimethyl-1,3-dioxolane-4-carboxylate (content of 82.2% calculated as free acid and 62% e.e. in R-form) in 90 ml of methanol. After crystallization the stirring was continued for 17 hours and the slurry was filtered over a sintered glass funnel. The product was dried for 17 hours at 30° C.

Yield: 6.8 g of calcium 2,2-dimethyl-1,3-dioxolane-4-carboxylate.3 $H_2O$ (content of 73.3% calculated as free acid and 98% e.e. in R-form).

EXAMPLE 7

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 7.0 g of sodium (R)-2,2-dimethyl-1,3-dioxolane-4-carboxylate and 3.0 g of potassium (S)-2,2-dimethyl-1,3-dioxolane-4-carboxylate (content of 81.7% calculated as free acid and with 43% e.e. in R-form) in 90 ml of methanol. After crystallization the stirring was continued for 17 hours and the slurry was filtered over a sintered glass funnel. The product was dried for 17 hours at 30° C.

Yield: 6.1 g of calcium 2,2-dimethyl-1,3-dioxolane-4-carboxylate.3 $H_2O$ (content of 73.1% calculated as free acid and 78% e.e. in R-form).

EXAMPLE 8

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 6.0 g of sodium (R)-2,2-dimethyl-1,3-dioxolane-4-carboxylate and 4.0 g of potassium (S)-2,2-dimethyl-1,3-dioxolane-4-carboxylate (content of 81.2% calculated as free acid and 23% e.e. in R-form) in 90 ml of methanol. After crystallization the stirring was continued for 17 hours and the slurry was filtered over a sintered glass funnel. The product was dried for 17 hours at 30° C.

Yield: 6.1 g of calcium 2,2-dimethyl-1,3-dioxolane-4-carboxylate.3 $H_2O$ (content of 71.2% calculated as free acid and 42% e.e. in R-form).

EXAMPLE 9

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 3.0 g of sodium (R)-2,2-dimethyl-1,3-dioxolane-4-carboxylate and 7.0 g of potassium (S)-2,2-dimethyl-1,3-dioxolane-4-carboxylate (content of 72.9% calculated as free acid and 35% e.e. in S-form) in 90 ml of methanol. After crystallization the stirring was continued for 17 hours and the slurry was filtered over a sintered glass funnel. The product was dried for 17 hours at 30° C.

Yield: 7.0 g of calcium 2,2-dimethyl-1,3-dioxolane-4-carboxylate.3 $H_2O$ (content of 66.1% calculated as free acid and 64% e.e. in S-form).

EXAMPLE 10

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 2.0 g of sodium (R)-2,2-dimethyl-1,3-dioxolane-4-carboxylate and 8.0 g of potassium (S)-2,2-dimethyl-1,3-dioxolane-4-carboxylate (content of 71.4% calculated as free acid and 53% e.e. in S-form) in 90 ml of methanol. After crystallization the stirring was continued for 17 hours and the slurry was filtered over a sintered glass funnel. The product was dried for 17 hours at 30° C.

Yield: 6.8 g of calcium 2,2-dimethyl-1,3-dioxolane-4-carboxylate.3 $H_2O$ (content of 59.4% calculated as free acid and 96% e.e. in S-form).

EXAMPLE 11

Crystallization of the calcium salt of 2,2-dimethyl-1,3-dioxolane-4-carboxylic acid A filtered solution of 3.63 g of anhydrous $CaCl_2$ in 30 ml of demineralized water was added at 20° C. to a clear, well stirred solution of a mixture of 1.0 g of sodium (R)-2,2-dimethyl-1,3-dioxolane-4-carboxylate and 9.0 g of potassium (S)-2,2-dimethyl-1,3-dioxolane-4-carboxylate (content of 70.0% calculated as free acid and 76% e.e. in S-form) in 90 ml of methanol. After crystallization the stirring was continued for 17 hours and the slurry was filtered over a sintered glass funnel. The product was dried for 17 hours at 30° C.

Yield: 9.0 g of calcium 2,2-dimethyl-1,3-dioxolane-4-carboxylate.3 H₂O (content of 58.8% calculated as free acid and 96% e.e. in S-form).

EXAMPLE 12

Recrystallization of the calcium salt of 2,2-dimethyl-1,3-dioxolane-4-carboxylic acid 4.1 g of calcium 2,2-dimethyl-1,3-dioxolane-4-carboxylate (content of 70% calculated as the free acid and 67% e.e. in R-form), was dissolved in 12 ml of refluxing methanol. The solution was filtered over a sintered glass funnel. The filter was washed with 5 ml of hot methanol. Crystallization was effected by cooling the solution to 25° C. while vigorously stirring. The product was isolated by filtration over a sintered glass funnel and dried at 25° C. in vacuo.

Yield: 1.8 g of calcium 2,2-dimethyl-1,3-dioxolane-4-carboxylate.3H₂O (content of 75.3% calculated as free acid and 92% e.e. in R-form).

EXAMPLE 13

Crystallization of the barium salt of 2,2-dimethyl-1,3-dioxolane-4-carboxylic acid A filtered solution of 10.9 g of BaBr₂.2H₂O in a mixture of 10 ml of demineralized water and 50 ml of methanol was added at 20° C. to a clear, well stirred solution of a mixture of 7.5 g of sodium (R)-2,2-dimethyl-1,3-dioxolane-4-carboxylate and 2.5 g of potassium (S)-2,2-dimethyl-1,3-dioxolane-4-carboxylate (content of 82.0% calculated as free acid and 52% e.e. in R-form) in a mixture of 10 ml of demineralized water and 40 ml of methanol. After the crystallization the stirring was continued for 48 hours and the slurry was filtered over a sintered glass funnel. The product was dried for 17 hours at 30° C.

Yield: 4.8 g of barium 2,2-dimethyl-1,3-dioxolane-4-carboxylate (content of 63.0% calculated as free acid and 92% e.e. in R-form).

EXAMPLE 14

Crystallization of the barium salt of 2,2-dimethyl-1,3-dioxolane-4-carboxylic acid A filtered solution of 10.9 g of BaBr₂.2H₂O in a mixture 10 ml of demineralized water and 50 ml of methanol was added at 20° C. to a clear, well stirred solution of a mixture of 2.5 g of sodium (R)-2,2-dimethyl-1,3-dioxolane-4-carboxylate and 7.5 g of potassium (S)-2,2-dimethyl-1,3-dioxolane-4-carboxylate (content of 79.5% calculated as free acid and 48% e.e. in S-form) in a mixture of 10 ml of demineralized water and 40 ml of methanol. After crystallization the stirring was continued for 48 hours and the slurry was filtered over a sintered glass funnel. The product was dried for 17 hours at 30° C.

Yield: 4.6 g of barium 2,2-dimethyl-1,3-dioxolane-4-carboxylate (content of 58.1% calculated as free acid and 94% e.e. in S-form).

EXAMPLE 15

Crystallization of the zinc salt of 2,2-dimethyl-1,3-dioxolane-4-carboxylic acid 18.0 g of ZnCl₂ was dissolved in 250 ml of methanol. To this mixture 50.0 g of crude sodium 2,2-dimethyl-1,3-dioxolane-4-carboxylate (content of 78.0 calculated as free acid and 79% e.e. in R-form) was added. After stirring stirring for 30 minutes the mixture was filtered. After addition of 750 ml of ethyl acetate to the filtrate, the resulting solution was concentrated using a steam bath until about 200 ml of solution was left. This solution was cooled to 5° C. and after 72 hours the NaCl precipitate was filtered off and the filtrate was concentrated to a volume of 125 ml and at 20° C. this solution was stirred for 18 hours. The formed crystals were filtered, washed with ethyl acetate and dried at 50° C. for 17 hours.

Yield: 23.0 of zinc 2,2-dimethyl-1,3-dioxolane-4-carboxylate (content of 79.0% calculated as free acid and 99% e.e. in R-form).

EXAMPLE 16

Recrystallization of the sodium salt of 2,2-dimethyl-1,3-dioxolane-4-carboxylic acid 1.50 g of sodium 2,2-dimethyl-1,3-dioxolane-4-carboxylate (content of 85.7% calculated as free acid and 78% e.e. in R-form) was dissolved in 50 ml of refluxing 1-propanol. Under vigorous stirring the solution was cooled to 25° C. The resulting slurry was stirred for 17 hours at this temperature and filtered over a sintered glass funnel. The product was washed with 10 ml of 1-propanol and acetone and dried for 24 hours at 50° C.

Yield: 0.60 g of sodium 2,2-dimethyl-1,3-dioxolane-4-carboxylate (content of 88.3% calculated as free acid and >98% e.e. in R-form). EXAMPLE 17

Recrystallization of the sodium salt of 2,2-dimethyl-1,3-dioxolane-4-carboxylic acid 1.50 g of sodium 2,2-dimethyl-1,3-dioxolane-4-carboxylate (content of 85.7% calculated as free acid and 78% e.e. in R-form) was dissolved in a refluxing mixture of 25 ml of acetonitrile and 16 ml of methanol. After cooling this solution to 25° C. and addition of 60 ml of acetone the vigorously stirred gelly solution crystallized. The slurry was stirred for 17 hours at 25° C. and isolated over a sintered glass funnel. The product was washed with acetone and dried for 24 hours at 50° C.

Yield: 0.68 g of sodium 2,2-dimethyl-1,3-dioxolane-4-carboxylate (content of 85.9% calculated as free acid and >98% e.e. in R-form).

EXAMPLE 18

Recrystallization of the sodium salt of 2,2-dimethyl-1,3-dioxolane-4-carboxylic acid 3.00 g of sodium 2,2-dimethyl-1,3-dioxolane-4-carboxylate (content of 85.7% calculated as free acid and 78% e.e. in R-form) was dissolved in 50 ml of refluxing absolute ethanol. After cooling this solution to 25° C. and addition of some crystals of sodium (R)-2,2-dimethyl-1,3-dioxolane-4-carboxylate the product crystallized rapidly and the resulting slurry was stirred for 17 hours at 25° C. The crystals were filtered over a sintered glass funnel, washed with 10 ml of ethanol and acetone and dried for 24 hours at 50° C.

Yield: 0.54 g of sodium 2,2-dimethyl-1,3-dioxolane-4-carboxylate (content of 86.2% calculated as free acid and >98% e.e. in R-form).

The addition of 175 ml of acetone to the mother liquor instantaneously resulted in a gelly mass that slowly crystallized. The slurry was stirred for a quarter of an hour, filtered over a sintered glass funnel. The product was washed with acetone and dried for 23 hours at 50° C.

Yield: 1.23 g of sodium 2,2-dimethyl-1,3-dioxolane-4-carboxylate (content of 86.4% calculated as free acid and >98% e.e. in R-form).

EXAMPLE 19

Recrystallization of the potassium salt of 2,2-dimethyl-1,3-dioxolane-4-carboxylic acid 5.00 g of potassium 2,2-dimethyl-1,3-dioxolane-4-carboxylate (content of 70.2% calculated as free acid and 78% e.e. in S-form) was dissolved in 25 ml of methanol. Subsequently 300 ml of acetone was added and stirring was continued for 30 minutes at 25° C. As no crystallization occured the solution was seeded with 20 mg of potassium (S)-2,2-dimethyl-1,3-dioxolane-4-carboxylate (content of 68.5% calculated as free acid and >98% e.e. in S-form). Within 5 minutes the product crystallized. It was isolated over a sintered glass funnel, washed with 5 ml of acetone and dried in vacuo for 17 hours at 25° C.

Yield: 1.92 g of potassium 2,2-dimethyl-1,3-dioxolane-4-carboxylate (content of 79.0% calculated as free acid and 92% e.e. in S-form).

EXAMPLE 20

Recrystallization of the magnesium salt of 2,2-dimethyl-1,3-dioxolane-4-carboxylic acid 1.00 g of magnesium 2,2-dimethyl-1,3-dioxolane-4-carboxylate (content of 80.3% calculated as free acid and 64% e.e. in R-form) was dissolved in 10 ml of methanol and subsequently 100 ml of acetone was added. The slurry was stirred for 48 hours, filtered over a sintered glass funnel and the crystals were dried in vacuo for 17 hours at 25° C.

Yield: 0.59 g of magnesium 2,2-dimethyl-1,3-dioxolane-4-carboxylate (content of 87.0% calculated as free acid and 80% e.e. in R-form).

EXAMPLE 21

Recrystallization of the magnesium salt of 2,2-dimethyl-1,3-dioxolane-4-carboxylic acid 5.00 g of magnesium 2,2-dimethyl-1,3-dioxolane-4-carboxylate (content of 80.3% calculated as free acid and 64% e.e. in R-form) was dissolved in 5 ml of hot methanol. Upon cooling the input crystallized rather completely. Another 5 ml of methanol was added and the mixture was heated to reflux. Surprisingly, not all the crystals could be dissolved this time. After cooling to 25° C. the slurry was stirred for 17 hours and subsequently filtered over a sintered glass funnel. The crystals were dried in vacuo for 17 hours at 25° C.

Yield: 1.25 g of magnesium 2,2-dimethyl-1,3-dioxolane-4-carboxylate (content of 82.4% calculated as free acid and 90% e.e. in R-form).

EXAMPLE 22

Crystallization of the calcium salt of 2,2-pentamethylene-1,3-dioxolane-4-carboxylic acid A filtered solution of 1.82 g of anhydrous $CaCl_2$ in 30 ml of demineralized water was added at 20° C. under vigorous stirring to a clear solution of 4.5 g of potassium (R)-2,2-pentamethylene-1,3-dioxolane-4-carboxylate and 0.5 g of racemic sodium 2,2-pentamethylene-1,3-dioxolane-4-carboxylate (the resulting mixture having a content of 69.0% calculated as free acid and 87% e.e. in R-form) in demineralized water. Crystallization started within a minute and after 90 minutes the product was filtered, washed with 10 ml of demineralized water and dried at 30° C. for 18 hours.

Yield: 3.2 g of calcium 2,2-pentamethylene-1,3-dioxolane-4-carboxylate.3 $H_2O$ (content of 79.2% calculated as free acid and 98% e.e. in R-form).

The percentage of R and S of the 2,2-pentamethylene-1,3-dioxolane-4-carboxylic acid or its salts was determined according to the following method. A solution of 20 mg of the salt in 1.0 ml of a phosphate buffer (pH=2.0) is extracted with 1.0 ml of $CDCl_3$ and filtered over $MgSO_4$. In the $^1H$-(360)-NMR spectrum of this solution the positions of the $C_4$-H, $C_5$-$H_1$ and $C_5$-$H_2$ are 4.62, 4.29 and 4.19 ppm respectively. After addition of 150 μl of a solution of R-(+)-1-(1-naphtyl)ethylamine (200 mg and 1.0 ml of $CDCl_3$) the positions of these protons shift to 4.11, 3.83 and 3.48 ppm for the R-isomer and to 4.08, 3.83 and 3.53 ppm for the S-isomer. However, these shifts appear to be very dependent on the relative concentrations of salt and added shift reagent.

EXAMPLE 23

Recrystallization of the calcium salt of 2,2-pentamethylene-1,3-dioxolane-4-carboxylic acid 2.10 g of calcium 2,2-pentamethylene-1,3-dioxolane-4-carboxylate (content of 79.9% calculated as free acid and 58% e.e. in R-form) was recrystallized from 15 ml of methanol. The solution was cooled to 25° C. and the resulting slurry was stirred for 17 hours. The product was filtered over a sintered glass funnel, washed with acetone and dried at 50° C. for 3 hours.

Yield: 1.34 g of calcium 2,2-pentamethylene-1,3-dioxolane-4-carboxylate.3 $H_2O$ (content of 80.5% calculated free acid and 80% e.e. in R-form).

1.23 g of this salt was recristallized from 25 ml of methanol. To initiate the crystallization two drops of demineralized water were added and the resulting slurry was stirred at 25° C. for 17 hours. The product was filtered over a sintered glass funnel, washed with acetone and dried at 50° C. for 3 hours.

Yield: 0.55 g of calcium 2,2-pentamethylene-1,3-dioxolane-4-carboxylate.3 $H_2O$ (content of 79.8% calculated as free acid and >98% e.e. in R-form).

EXAMPLE 24

Recrystallization of the calcium salt of 2,2-pentamethylene-1,3-dioxolane-4-carboxylic acid A slurry of 0.48 g of calcium 2,2-pentamethylene-1,3-dioxolane-4-carboxylate (content of 79.9% calculated as free acid and 58% e.e. in R-form) in 2.5 ml of methanol was stirred at 25° C. for 17 hours. The slurry was filtered over a sintered glass funnel, washed with acetone and dried at 25° C. for 3 hours.

Yield: 0.23 g of calcium 2,2-pentamethylene-1,3-dioxolane-4-carboxylate.3 $H_2O$ (content of 80.8% calculated as free acid and 96% e.e. in R-form).

We claim:

1. A process for preparing a 2,2-$R_1$, $R_2$-1,3-dioxolane-4-carboxylic acid or salt thereof rich in either the R or S enantiomer which process comprises
   a) preparing a solution which contains a non-racemic mixture of R and S enantiomer of a carboxylate of the formula

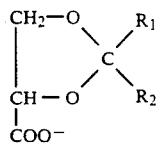

and $M^{n+}$ ions, wherein $R_1$ and $R_2$ are each independently, H or an alkyl group, or $R_1$ and $R_2$, together with the carbon atom to which they are attached, form a carbocylic ring, and M is an alkali metal, an alkaline earth metal, a group IIb metal, and n is the valency of M;

b) reducing the solubility of the $M^{n+}$ salt of compound (I); and c) separating the resulting crystals from the mother liquor.

2. A process according to claim 1 which further comprises adding seeding crystals to the mixture during or after step b).

3. A process according to claim 1 wherein $R_1$ and $R_2$ are each, independently, a branched or unbranched $C_1$-$C_6$ alkyl group, or $R_1$ and $R_2$, together with the carbon atoms to which they are attached, form a carbocyclic ring containing 8 carbon atoms or less.

4. A process according to claim 1, wherein $R_1$ and $R_2$ are each, independently, a branched or unbranched $C_1$-$C_4$ alkyl group or $R_1$ and $R_2$ together with the carbon atoms to which they are attached, form a carbocyclic ring containing 5 or 6 carbon atoms.

5. A process according to claim 1, wherein $R_1$ and $R_2$ are each methyl.

6. A process according to claim 1, wherein M is Na, K, Ca, Mg, Zn or Ba.

* * * * *